United States Patent
Lee et al.

(10) Patent No.: US 10,143,705 B2
(45) Date of Patent: Dec. 4, 2018

(54) METHOD OF TREATING A PATIENT WITH A DISEASE CAUSED BY A PATHOGENIC MECHANISM ASSOCIATED WITH ACCUMLATION OF METHYLGLYOXAL

(71) Applicant: Jen-Ai Lee, Taipei (TW)

(72) Inventors: Jen-Ai Lee, Taipei (TW); Yi-Chieh Li, Taipei (TW)

(73) Assignee: Jen-Ai Lee, Taipei (TW)

( * ) Notice: Subject to any disclaimer, the term of this patent is extended or adjusted under 35 U.S.C. 154(b) by 0 days.

(21) Appl. No.: 15/664,221

(22) Filed: Jul. 31, 2017

(65) Prior Publication Data

US 2017/0326170 A1 Nov. 16, 2017

Related U.S. Application Data

(62) Division of application No. 15/057,291, filed on Mar. 1, 2016.

(30) Foreign Application Priority Data

Mar. 10, 2015 (TW) .............................. 104107513 A

(51) Int. Cl.
*A61K 31/722* (2006.01)
*A61K 31/7008* (2006.01)

(52) U.S. Cl.
CPC ........ *A61K 31/722* (2013.01); *A61K 31/7008* (2013.01)

(58) Field of Classification Search
None
See application file for complete search history.

(56) References Cited

U.S. PATENT DOCUMENTS

2009/0226545 A1 9/2009 Blotsky

FOREIGN PATENT DOCUMENTS

WO 2009126145 A1 10/2009

OTHER PUBLICATIONS

Zhang, J. et al., Marine Drugs, "Chitosan Modification and Pharmaceutical/Biomedical Applications", 2010, vol. 8, pp. 1962-1987.*
Ya-Min Chang, et al., "Effects of low molecular weight chitosans on aristolochic acid-induced renal lesions in mice", Food Chemistry, Elsevier Ltd., NL, vol. 129, No. 4, Jun. 23, 2011 (Jun. 23, 2011) pp. 171-1758, XP028262764.
Anandan R., et al. "Antiaging effect on dietary chitosan supplementation on glutathione-dependent antioxidant system in young and aged rats," Cell Stress and Chaperones; A Comprehensive Journal of Stress Biology and Medicine, Springer Netherlands, Dordrecht, vol. 18, No. 1, Jul. 25, 2012 pp. 121-125, XP035145272.
Hanaa M Abd El-Fattah et al, "Chitosan as a Hepato-Protective Agent Against Single Oral Dose of Dioxin," IOSR Journal of Environmental Science, Toxicology and Food Technology, vol. 7, No. 3, Nov. 2013, pp. 11-17, XP002758718.
Weimer Sandra et al: "D-Glucosamine Supplementation extends life span of nematodes and of aging mice," Nature Communications, vol. 5, Apr. 2014, XP002758719.
Mattiello-Sverzut Ana Claudia, et al. "Morphological adaptation of muscle collagen and receptor of advanced glycation end product (RAGE) in osteoarthritis patients with 12 weeks of resistance training; influence of anti-inflammatory of glucosamine treatment," Rheumatology International, vol. 33, No. 9, Sep. 2013, p. s2215-2224, XP002758720.
Anonymous: "Glucosamine protects against cancer, heart disease and death from all causes in new landmark study", Internet, Nov. 29, 2012, XP002758721.
Chang, Y.M, et al, Food Chemistry "Effects of low molecular weight chitosans on aristolochic acid-induced renal lesions in mice", 2011, vol. 129, pp. 1751-1758.

* cited by examiner

*Primary Examiner* — Shaojia A Jiang
*Assistant Examiner* — Bahar Craigo
(74) *Attorney, Agent, or Firm* — Bacon & Thomas, PLLC

(57) ABSTRACT

The present invention discloses a method comprising administering a monosaccharide and/or polysaccharide as an active ingredient, for decreasing the accumulation of dicarbonyl compounds in the human body. Said monosaccharide is a monomer of said polysaccharide, and the molecular weight of the polysaccharide ranges from 29 kDa to 36 kDa. The monosaccharide and/or polysaccharide can be used to prevent or treat nephritis or diseases associated with dicarbonyl compounds, or other diseases caused by carbonyl-stress, and can also be used to make the relevant drug.

2 Claims, 7 Drawing Sheets

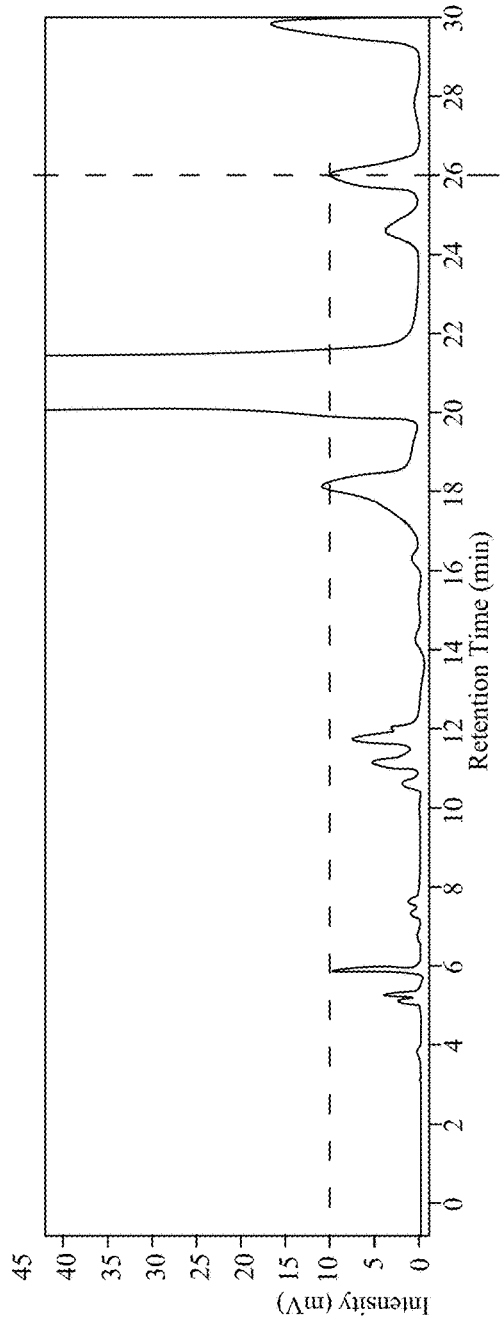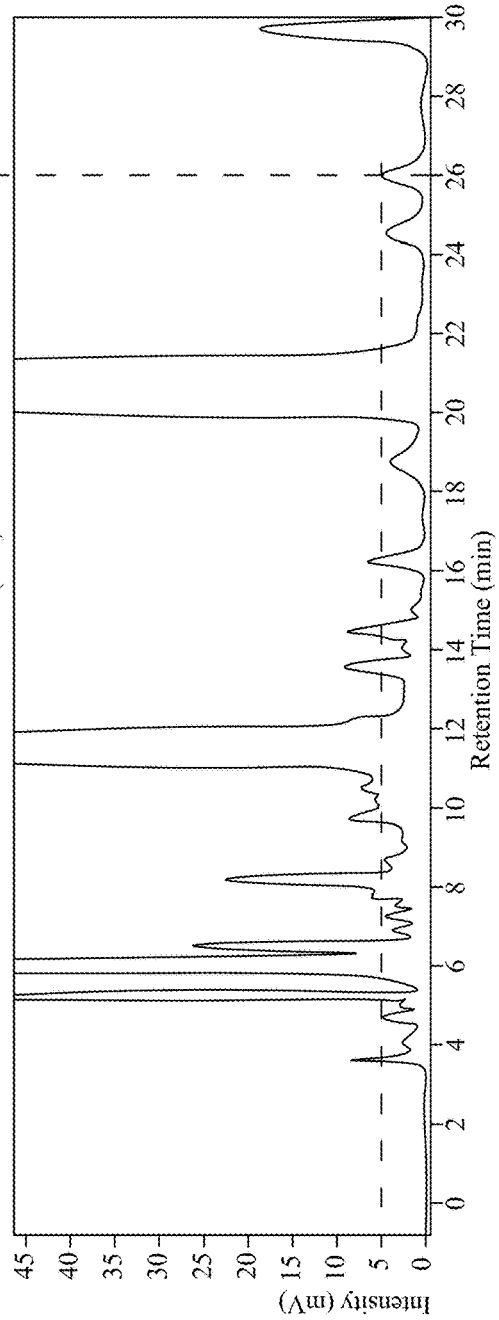

METHOD OF TREATING A PATIENT WITH A DISEASE CAUSED BY A PATHOGENIC MECHANISM ASSOCIATED WITH ACCUMLATION OF METHYLGLYOXAL

CROSS REFERENCE TO RELATED APPLICATION

This application is a divisional application of U.S. patent application Ser. No. 15/057,291, filed on Mar. 1, 2016, entitled "PHARMACEUTICAL COMPOSITION COMPRISING MONOSACCHARIDE AND/OR POLYSACCHARIDE AND USES OF MONOSACCHARIDE AND POLYSACCHARIDE", which claims priority to TW Application No. 104107513, filed on Mar. 10, 2015, both of which are hereby incorporated by reference in their entirety.

BACKGROUND OF THE INVENTION

(1) Field of the Invention

The present invention relates to novel medical application of a monosaccharides and/or polysaccharides, particularly for those using the monosaccharides and polysaccharides in pharmaceutical composition production and usage for reducing methylglyoxal.

(2) Description of the Prior Art

Many studies demonstrate that di-carbonyl compounds relates to some diseases such as diabetic, arthritis, or aging process of rest parts in the human body as it can induce protein glycation, resulting in cell damage and dysfunction. In the process of tissue repair when human body is injured, additional energy required in tissue repair is obtained from decomposition of carbohydrate, fat or protein. Di-carbonyl compounds such as methylglyoxal (also known as MG) or glyoxal and so like are byproducts in the decomposition of carbohydrate, fat or protein, which are also reactants of carbonyl compounds and amino acid compounds. Taking diabetics as example, increase of the blood glucose inductively causes increase in the frequency of glycation, which incurs secondary damage of human body due to carbonyl-stress induced by the di-carbonyl compounds. Moreover, carbonyl-stress is also the primary factor for producing oxidative-stress of the human body, and the oxidative-stress induced by the methylglyoxal will cause cell damage subsequently.

The glycation process will produce many advanced glycation end-products (also known as AGEs). Methylglyoxal includes two aldehydes, which are reactants from its non-enzyme reactions to protein by conjugating with free amino (—$NH_2$) and mercapto (—SH) of the protein. Due to strong conjugating capability of the methylglyoxal with protein, which also means strong glycating capability of the methylglyoxal to protein, the protein modification caused by the methylglyoxal not only can change the biological activity of the glycated protein but also can produce advanced glycation end-products, wherein the $N^\varepsilon$-(carboxyethyl)lysine (also known as CEL) is one ingredient of major advanced glycation end-products. For diabetics, the content level of the $N^\varepsilon$-(carboxyethyl)lysine will be increased. Some studies demonstrate that the molecular mechanism mutually caused by the methylglyoxal and $N^\varepsilon$-(carboxyethyl)lysine also involves in renal damage associated while some other studies illustrate that the neuralgia impacted by the methylglyoxal is worse than neuralgia impacted by the blood sugar to the diabetics. Therefore, regulating the content level of the methylglyoxal is a vital preventive means for the complication evolution to the diabetics.

Currently, several pharmacological interventions for preventing methylglyoxal-related injuries have been proposed and tested such as several chemical agents by protein modification to intervene the function of the methylglyoxal while several other chemical agents including thiamine and aminoguanidine by reducing the content level of the methylglyoxal. However, most of these agents cannot be used for treatment because of their toxicity, instability, or low potency. Among all the available agents, only metformin is widely used for the treatment of diabetes and for lowering blood sugar. To date, only one effective methylglyoxal reducing agent has been approved by the US Food and Drug Administration (known as FDA) is metformin, whose major ingredient is metformin hydrochloride.

Accordingly, for better prevention of the diabetes complications and treatments of other related damages or aging process, developing an effective anti-methylglyoxal agent is urgently needed.

SUMMARY OF THE INVENTION

One object of the present invention is to provide a method for reducing di-carbonyl compounds in a patient by using active ingredients include monosaccharides and/or polysaccharides.

Another object of the present invention is to provide an usage of monosaccharides and/or polysaccharides for using in treating a patient with a disease caused by a pathogenic mechanism associated with accumulation of di-carbonyl compounds.

In order to effectively achieve foregoing objects, the present invention provides a method of treating a patient with a disease caused by a pathogenic mechanism associated with accumulation of methylglyoxal, the method comprising: administering an effective amount of polysaccharide to the patient suffering from the disease to reduce a content level of methylglyoxal in the patient, wherein the disease is selected from a group consisting of heart disease, arthritis, cataract and cancer, and said polysaccharide has a range of molecular weight from 29 kDa to 36 kDa, and has a monomer with a molecular structure shown as below:

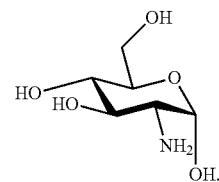

In an exemplary embodiment of the present invention, the polysaccharide is chitosan with the range of molecular weight from 29 kDa to 36 kDa.

In an exemplary embodiment of the present invention, the polysaccharide has a reducing ratio to inhibit the methylglyoxal over 50% when the polysaccharide reaches a concentration of 4.60 µg·mL$^{-1}$ in a mouse body.

In an exemplary embodiment of the present invention, the polysaccharide has a range of reducing ratio of the methylglyoxal between 50% and 70% when the polysaccharide has a concentration range between 4.60 µg·mL$^{-1}$ and 30.00 µg·mL$^{-1}$ in a mouse body.

In an exemplary embodiment of the present invention, the effective amount of the polysaccharide for the patient is converted according to an effective dosage 500 mg·kg$^{-1}$·d$^{-1}$ in a mouse body if the polysaccharide is continuously delivered for 14 days.

In an exemplary embodiment of the present invention, the method further comprises: administering the effective amount of the polysaccharide to the patient to reduce a content level of an advanced glycation end-products.

In an exemplary embodiment of the present invention, the polysaccharide has a conjugation bonding duration with methylglyoxal reaches to 24 hours under temperature 37 degree centigrade in a mouse body.

Besides, the present invention provides a A method of treating a patient with a disease caused by a pathogenic mechanism associated with accumulation of methylglyoxal, the method comprising: administering an effective amount of monosaccharide to a patient suffering from the disease to reduce a content level of methylglyoxal in the patient, wherein the disease is selected from a group consisting of liver disease, kidney disease, diabetic complications, cataract and chronic renal failure, and said monosaccharide has a molecular structure shown as below:

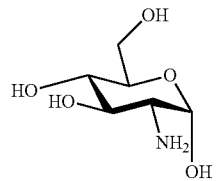

In an exemplary embodiment of the present invention, the monosaccharide is glucosamine.

From all foregoing exemplary embodiments, it is apparent that the function of the monosaccharides and/or polysaccharides not only has reducing capability of methylglyoxal but also has scavenging capability in accumulation of methylglyoxal and advanced glycation end products. For nephropathy and other diseases associated with pathogenic mechanism of the methylglyoxal, as well as other diseases induced by the carbonyl stress, the monosaccharides and/or polysaccharides is a novel preventive and treatment modality. Other than that, the monosaccharides and/or polysaccharides can also be used to produce relevant agents accordingly.

BRIEF DESCRIPTION OF THE DRAWINGS

FIGS. 1A and 1B show inhibitory effects for the monosaccharides against methylglyoxal in vitro.

DESCRIPTION OF THE PREFERRED EMBODIMENTS

Figure 1:
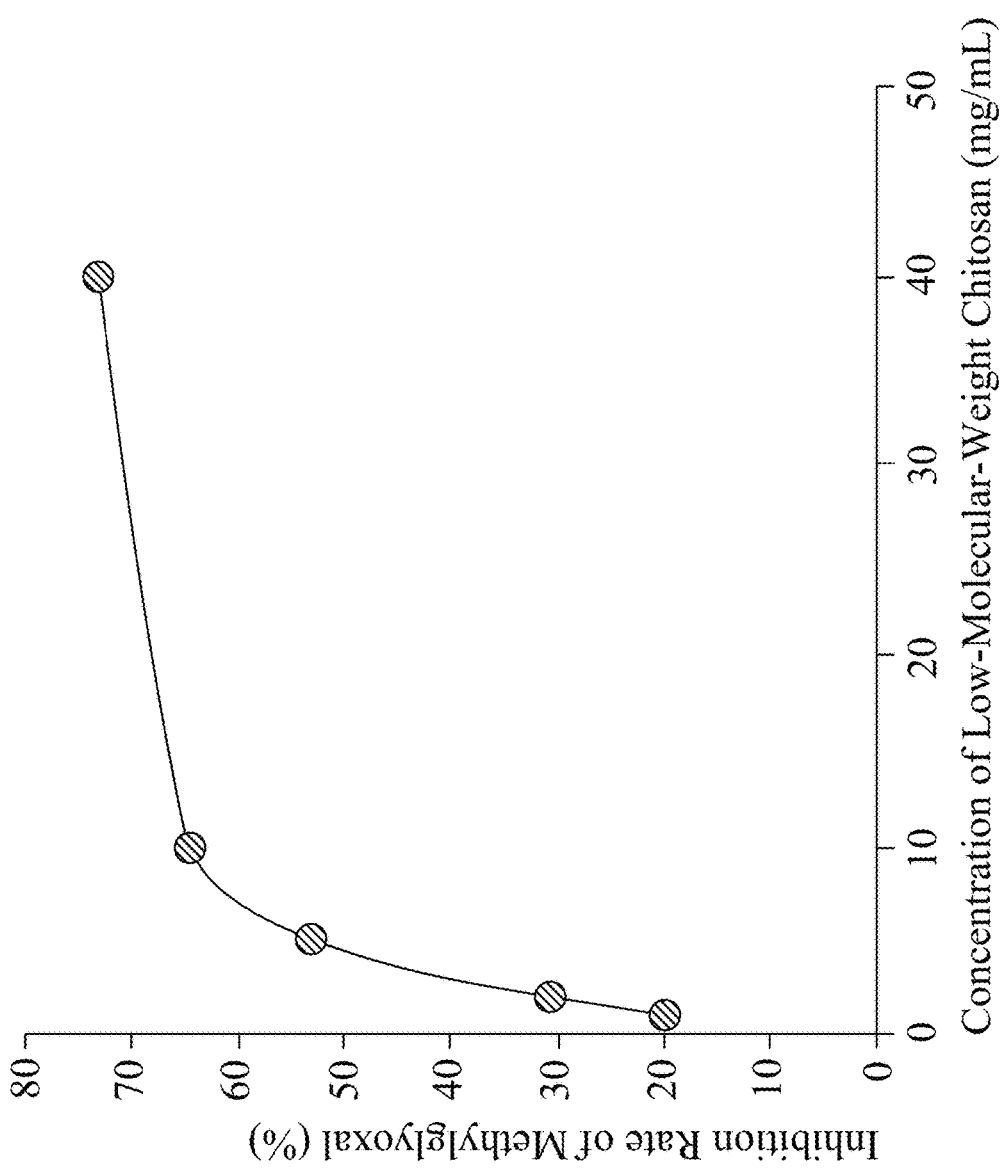
FIG. 1 illustrates an inhibition rate curve showing inhibitory effect for the low-molecular-weight chitosan against methylglyoxal in vitro.

Regarding technical contents, features and effects disclosed above and other technical contents, features and effects of the present invention will be clearly presented and manifested In the following detailed description of the exemplary preferred embodiments with reference to the accompanying drawings which form a part hereof.

Chitosan is a natural polysaccharide including chitin with de-acetylation degree over 55% normally. Generally, chitosan features with a high molecular weight (500-1,000 kDa) and low solubility. The high-molecular-weight chitosan can be hydrolyzed into low-molecular-weight chitosan (also referred to as "LMW-chitosan") with a molecular weight about 29 kDa to 36 kDa, and therefore it can be utilized in the present invention. The low-molecular-weight chitosan is highly water-soluble with molecular structural formula shown as below:

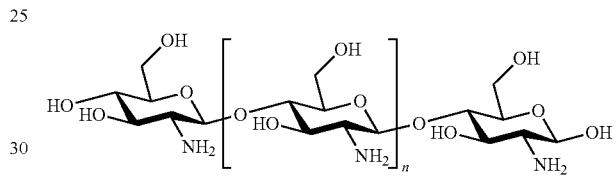

Wherein, the range for the parameter n in foregoing molecular structural formula of the low-molecular-weight chitosan is 10 thousands to 800 thousands.

The monomer of the low-molecular-weight chitosan is glucosamine with molecular structural formula shown as below:

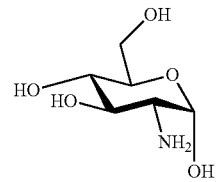

Following disclosures are based on the low-molecular-weight chitosan to serves as an exemplary embodiment for the purpose in elucidating producing method, new usages and associated effects thereof. However, other monosaccharide has same functional groups as low-molecular-weight chitosan or monomer of the low-molecular-weight chitosan also has similar usages and associated effects.

Exemplary Embodiment 1: The Preparation of Chitosanase and Low-Molecular-Weight Chitosan The chemicals used in the present invention include crab shell chitosan (84% deacetylated degree; approximately 1,100 kDa); an advanced glycation end products (also known as AGEs) reagents kit; a glutathione assay kit; an anti-advanced glycation end products antibodies; and a polymer detection system. In an exemplary embodiment, the primary advanced glycation end product is N$^\varepsilon$-(carboxyethyl)lysine (also known as CEL).

The high-molecular-weight chitosan is used to induce green bamboo shoots for producing chitosanase. The chitosanase is in turn utilized to digest high-molecular-weight chitosan with molecular weight 1,100 kDa into low-molecular-weight chitosan with molecular weight about 29 kDa.

Briefly, green bamboo shoots are coated with high-molecular-weight chitosan and stored in an environment under temperature at 25 degree centigrade to induce chitosanase. Then the chitosanase is isolated to measure its activity. Chitosan is suspended acetic acid with 4.5% concentration for being digested with 180 unit chitosanase under temperature at 50 degree centigrade for 18 hours, and being purified before use.

Exemplary Embodiment 2: Assaying the Inhibitory Effect for the Low-Molecular-Weight Chitosan Against Methylglyoxal (Also Known as MG) In Vitro Firstly, put sodium phosphate buffer (0.2 M, pH=7.4) into methylglyoxal or mixture of methylglyoxal and low-molecular-weight chitosan to become a resultant. Secondly, incubate the resultant under temperature of 37 degree centigrade for 24 hours. And finally, assay the content level of methylglyoxal in the resultant by means of high-performance liquid chromatography (also known as HPLC).

FIG. 1 illustrates an inhibition rate curve showing inhibitory effect for the low-molecular-weight chitosan against methylglyoxal in vitro. Wherein, the inhibitory effect is accomplished by the binding of low-molecular-weight chitosan with methylglyoxal in vitro, for example, methylglyoxal chelation and inhibition by low-molecular-weight chitosan. The inhibition rate or reducing ratio of low-molecular-weight chitosan against methylglyoxal is over 50% when a concentration of the low-molecular-weight chitosan reaches to 4.60 μg·mL$^{-1}$. It demonstrates that the low-molecular-weight chitosan in low concentration has good inhibitory effect against methylglyoxal.

Exemplary Embodiment 3: Assaying the Inhibitory Effect for the Monosaccharides Against Methylglyoxal In Vitro FIGS. 1A and 1B show inhibitory effects for the monosaccharides against methylglyoxal in vitro, wherein FIG. 1A shows the content level of methylglyoxal while FIG. 1B shows left quantity of methylglyoxal after the combination of the monosaccharides with methylglyoxal. The percentage inhibitory ratio of monosaccharide against methylglyoxal is 50% when the concentration of the monosaccharide is 0.05 M.

Exemplary Embodiment 4: Determination the Content Level of the Methylglyoxal in Kidney Samples In this and following exemplary embodiments, the animal treatment and sample preparation are performed as below. A total of 23 six-week-old female C3H/He mice are purchased from the National Laboratory Animal Breeding and Research Center (Taipei, Taiwan). The mice are divided into a control group (hereinafter referred to as Group C) consisting of five mice and three testing groups of six mice each after 1 week of acclamation, wherein the three testing groups are disease group (hereinafter referred to as Group A), low-molecular-weight chitosan only group (hereinafter referred to as Group M) and therapy group (hereinafter referred to as Group AM). The control group (Group C) and low-molecular-weight chitosan only group (Group M) are injected with 0.1 mL normal saline each day for 5 days (days 1-5) by means of intraperitoneal injection (IP), whereas the disease group (Group A) and therapy group (Group AM) are injected with 0.1 mL 10 mg kg$^{-1}$ aristolochic acid (also known as AA) by means of intraperitoneal injection each day for 5 days. After aristolochic acid injection, the mice in Group AM and Group M then received low-molecular-weight chitosan 500 mg kg$^{-1}$ day$^{-1}$) per os for 14 days, which equals that the human body receives low-molecular-weight chitosan 87.52 mg kg$^{-1}$ day$^{-1}$ per person substantially, whereas mice in Groups C and A received the same volume of water.

In this and following exemplary embodiments, all data in the statistical analysis are expressed as means±standard errors of the means (also known as SEMs, where n≤5). Whereas, the differences are analyzed using one-way analysis of variance (also known as ANOVA), and the levels of significance among various treatments are determined by means of Scheffe's multiple range test such that differences with p values<0.05 are considered statistically significant.

Subsequently, the kidneys of experiment mice are homogenized and diluted with phosphate buffered saline (also known as PBS) so that resulting diluted kidney homogenate samples are obtained to detect the methylglyoxal (MG) level. To determine the methylglyoxal levels in the he kidneys of experiment mice, the high-performance liquid chromatography is applied. The derivatization of the diluted kidney homogenate samples is further performed by putting into ammonium chloride buffer (NH$_4$Cl, pH=10) and derivative reagent of diaminedichloroplatinum (II) (also known as DDP, 7.5×10$^{-4}$ M) therein. After derivatization, the kidney homogenates are layered onto a column of octadecylsilyl group (also known as ODS) with dimensions of (250 mm×4.6 mm inside diameter; 5 μm particle size) for separation. Then, acetonitrile is used as the mobile phase in addition to citric acid buffer (0.01 M) such that the ratio of volume/volume=3:97, flow rate=0.7 mL/min and the ratio of light excitation/emission (Ex/Em)=330/500 nm.

Figure 2:
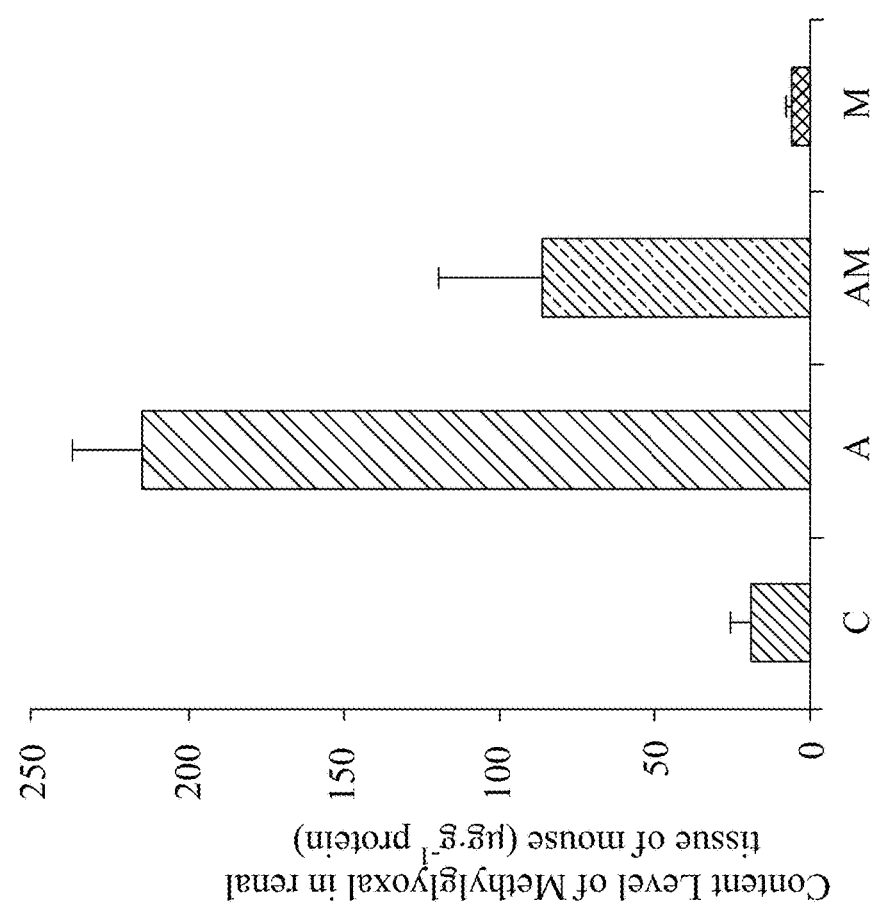
FIG. 2 shows inhibitory effect for the content level of low-molecular-weight chitosan to methylglyoxal in renal tissue of experiment mouse model.

FIG. 2 shows inhibitory effect for low-molecular-weight chitosan to the content level of methylglyoxal in renal tissue of experiment mouse. The methylglyoxal levels in the in vivo study are ascertained by high-performance liquid chromatography and then normalized with protein assay. In this exemplary embodiment, the methylglyoxal levels in the kidneys of Group A mice are significantly higher than those in Group C mice (212.86±24.34 vs. 18.23±8.05 μg g$^{-1}$ protein, respectively, p<0.05). Whereas, FIG. 2 shows that for mice in Group AM, treatment with low-molecular-weight chitosan decrease methylglyoxal levels to 86.15±33.79 μg g$^{-1}$ protein (p<0.05 vs. Group A).

The experiment mice are grouped and treated as below: Group C denotes to control group, whose mice are normally controlled for comparative contrast; Group A denotes to disease group, whose mice are treated with aristolochic acid to be infected by the aristolochic acid nephropathy (also known as AAN); Group M denotes to LMW-Chitosan group, whose mice are treated with low-molecular-weight chitosan only; and Group AM denotes to therapy group, whose mice are treated with low-molecular-weight chitosan after aristolochic acid nephropathy having infected. FIG. 2 illustrates that treatment with low-molecular-weight chitosan significantly decreased renal methylglyoxal accumulation in the aristolochic acid-induced nephropathy.

Exemplary Embodiment 5: Determination the Content Level of the Advanced Glycation End Products in Kidney Samples Briefly for sample preparation, all kidney homogenate samples are diluted in phosphate buffered saline to a final total protein content level of 10 μg mL$^{-1}$. And one hundred microliters of each sample or standard is then added to a protein adsorbent plate, which is incubated overnight under temperature at 4 degree centigrade. After incubation, the protein adsorbent plate is rinsed with phosphate buffered saline twice and subsequently incubated with 200 μL Assay Diluent buffer for 1.5 hour, and the protein adsorbent plate is then rinsed three times with 250 μL wash buffer and incubated with anti-Nε-(carboxyethyl)lysine antibodies at room temperature for 1 hour on an orbital shaker. Then the protein adsorbent plate is again rinsed with wash buffer three times and incubated with secondary horseradish peroxidase-conjugated antibodies for 1.5 hour at room temperature on an orbital shaker. Next, the protein adsorbent plate is rinsed with wash buffer five times and then incubated with 100 μL substrate solution at room temperature for 15 min on an orbital shaker. Finally, the enzyme reaction is stopped by adding 100 μL stop solution to each well. Consequently, the absorbances of the reaction mixtures were read immediately on a microplate reader at 450 nm.

Figure 3:
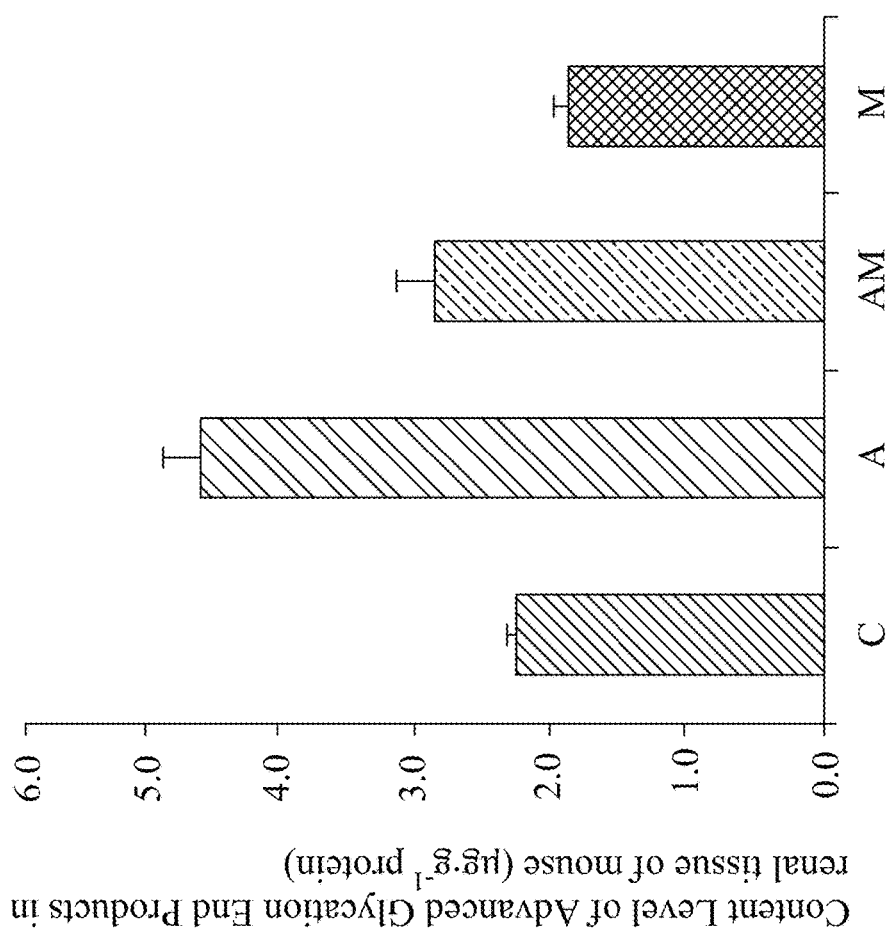
FIG. 3 shows inhibitory effect for low-molecular-weight chitosan to the quantitative data of advanced glycation end products in renal tissue of experiment mouse model.

FIG. 3 shows inhibitory effect for low-molecular-weight chitosane to the quantitative data of advanced glycation end products in renal tissue of experiment mouse. Wherein, the levels of advanced glycation end products in Group A mice are significantly higher than those in Group C mice (4.6±0.27 vs. 2.24±0.08 μmol/μg protein, respectively). After low-molecular-weight chitosane treatment, the level of advanced glycation end products in Group AM mice decreased to 2.84±0.28 μmol/μg protein (p<0.05 vs. Group A). Apparently, the level of advanced glycation end products in Group A mice of aristolochic acid nephropathy is almost double as that in Group C mice while the level of advanced glycation end products in Group AM mice is reversibly backed to original level after having been treated by the suitable quantity of low-molecular-weight chitosan.

Exemplary Embodiment 6: Immunohistological Staining of the Advanced Glycation End Products and Histological Assaying for the Pathological Changes in Kidney Disease Briefly for further preparation of kidney samples, the mouse kidneys are fixed with 4% paraformaldehyde for 2 days, and dehydrated with different concentrations of ethanol and xylene, then embedded in paraffin, and sectioned to 5 μm thick for immunohistochemistry study to determine the localization thereof. After blocking endogenous peroxidase activity by treating the sections with 3% peroxide ($H_2O_2$) for 10 minutes, the sample-lading slides are rinsed three times with phosphate buffered saline, then, the sample-lading slides are incubated with blocking reagent A for 60 minutes at room temperature. Next, anti-advanced glycation end products antibodies are diluted 50-fold and incubated with the samples overnight, followed by rinsing with phosphate buffered saline, and the kidney samples are incubated with blocking reagent B for 10 minutes at room temperature. Subsequently, the kidney samples are incubated with a secondary antibody for 10 min at room temperature, and the tissue sections are rinsed for three times and then dried carefully. Wherein, the secondary antibody is a reductive Fab's fragment from bonding resultant of a marked polymer and goat anti-mouse (also known as IgG), whereas, the marked polymer is prepared by combination of amino acid polymer and multiple molecules peroxidase. Two drops of the chromogen/substrate reagent is added to each sample section, and the kidney samples were incubated in the dark at room temperature for 10 minutes. The cell nuclear in sample section is then counterstained with hematoxylin. Moreover, staining without inclusion of the primary antibody is performed as the negative control.

Figure 6:
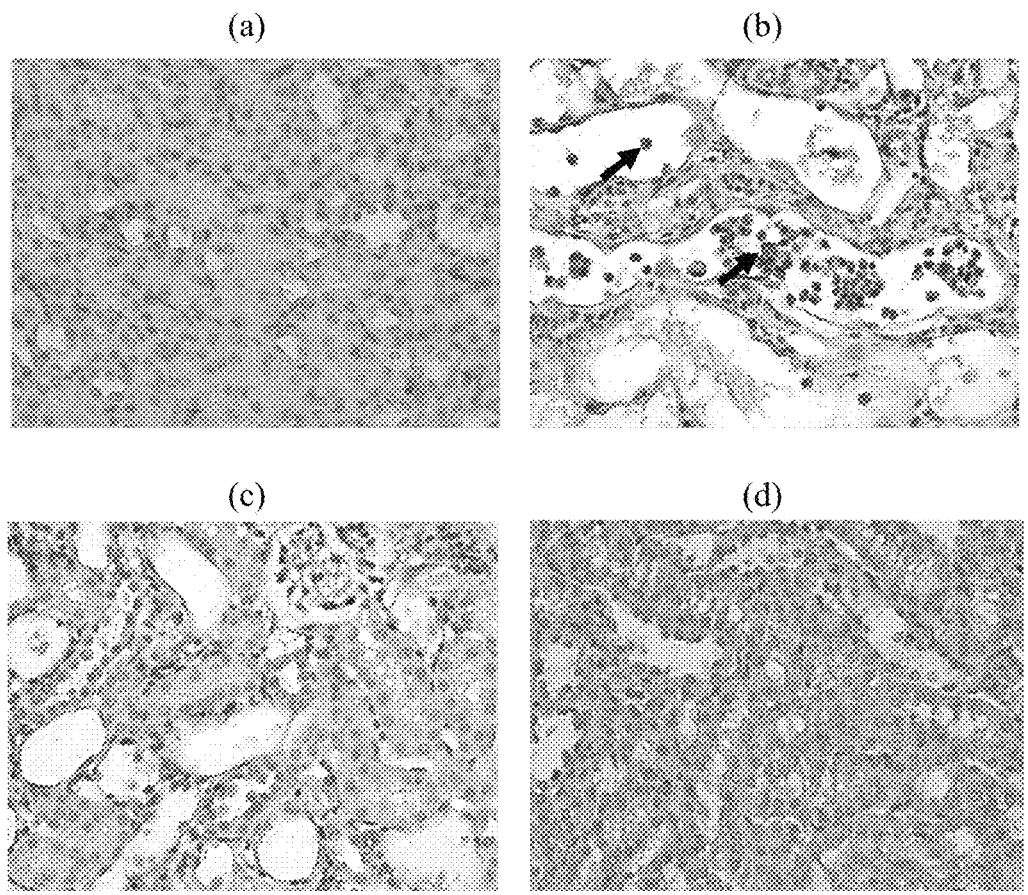
FIG. 6 shows pictures (a) to (d) of visualized expression for the advanced glycation end products in the kidney samples.

The pictures (a) to (d) in the FIG. 6 show visualized expression for the advanced glycation end products in the kidney samples. As previously defined, the experiment mice are grouped and treated as below: Group C denotes to control group as shown in picture (a), whose mice are normally controlled for comparative contrast; Group A denotes to disease group as shown in picture (b), whose mice are treated with aristolochic acid to be infected by the aristolochic acid nephropathy; Group M denotes to LMW-Chitosan group as shown in picture (d), whose mice are treated with low-molecular-weight chitosan only; and Group AM denotes to therapy group as shown in picture (c), whose mice are treated with low-molecular-weight chitosan after aristolochic acid nephropathy having infected. We observed that the advanced glycation end products immunohistological staining is present in several monocytes of the desquamation tubule region (as indicated by arrowhead) and that low-molecular-weight chitosan treatment significantly decreased the level of advanced glycation end products staining.

Exemplary Embodiment 7: Determination of Glutathione Concentrations in Kidney Samples To determine the glutathione concentrations or glutathione levels in kidney samples, a glutathione assay kit is applied for measurement. For facilitating measurement, the glutathione assay kit uses the reaction between glutathione sulfhydryl groups and 5,5'-dithio-bis-(2-nitrobenzoic acid) (also known as DTNB), yielding yellow 5-thio-2-nitrobenzoic acid (also known as TNB), which can be easily detected. Briefly for the process, the protein of the tissue kidney homogenates is firstly removed, then the de-protein kidney homogenates are added to a mixed reagent (also referred to as "cocktail"), which comprises a MES buffer, mixture cofactors, glutathione reductase, glucose-6-phosphate dehydrogenase and 5,5'-dithiobis-(2-nitrobenzoic acid). Wherein, the MES buffer includes 2-(N-morpholino) ethanesulfonic acid (0.2 M), phosphate (0.05 M) and ethylenediamine tetra-acetic acid (also known as EDTA: 1 mM; pH=6.0) while the mixture cofactors includes NAPH and glucose-6-phosphate. The mixture reagent is incubated under temperature at 37 degree centigrade in the dark, and the absorbance is measured at 405 nm at 5-minute intervals over 30 minutes. Consequently, calculate the glutathione concentrations in kidney samples by criterion means of Glutathione disulfide (also known as GSSG).

Figure 4:
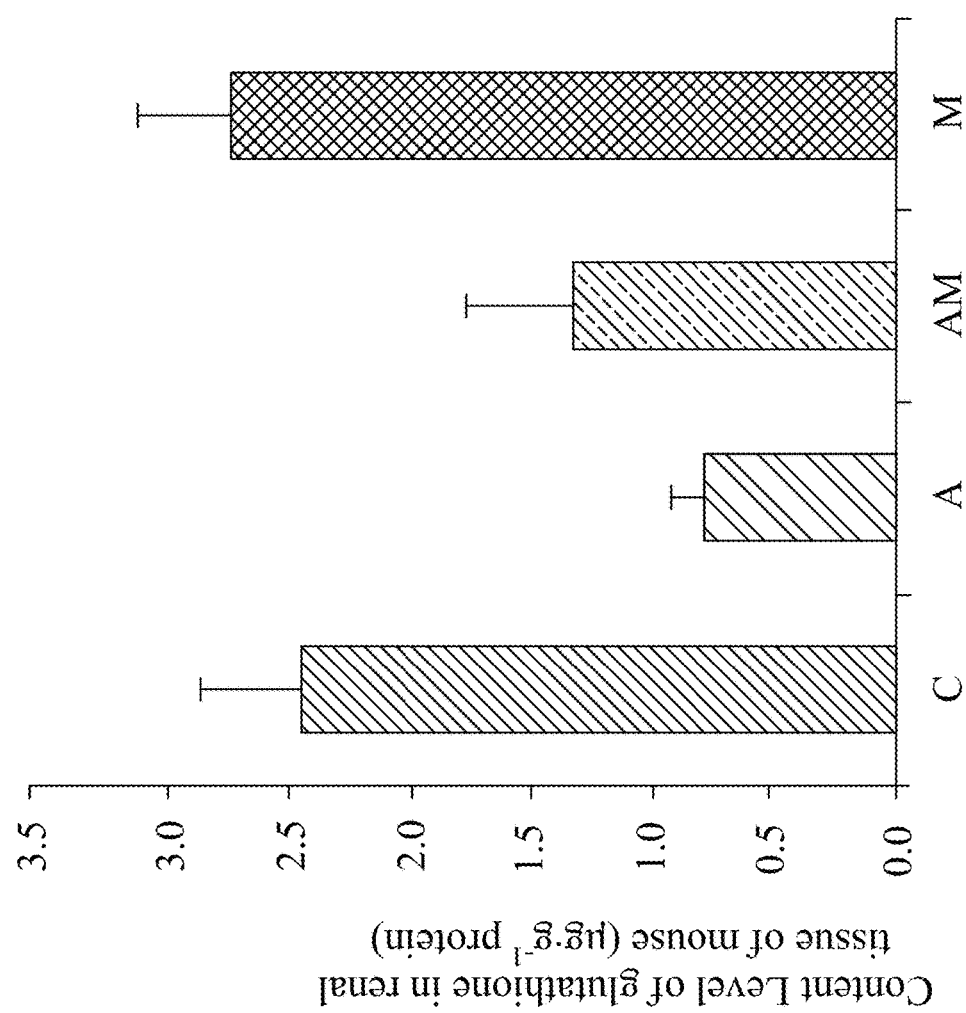
FIG. 4 shows inhibitory effect for low-molecular-weight chitosan to the content level of glutathione in renal tissue for the disease group A of experiment mouse model.

FIG. 4 shows effects of low-molecular-weight chitosan on glutathione levels in the kidneys. The intrarenal glutathione levels in Group A mice are lower than those in Group C mice (0.78±0.15 vs. 2.46±0.41 μg g$^{-1}$ protein, respectively; p<0.05). However, glutathione levels does not recover significantly after administration of low-molecular-weight chitosan treatment (Group AM: 1.31±0.46 μg g$^{-1}$ protein, p>0.05 vs. Group A mice).

Figure 5:
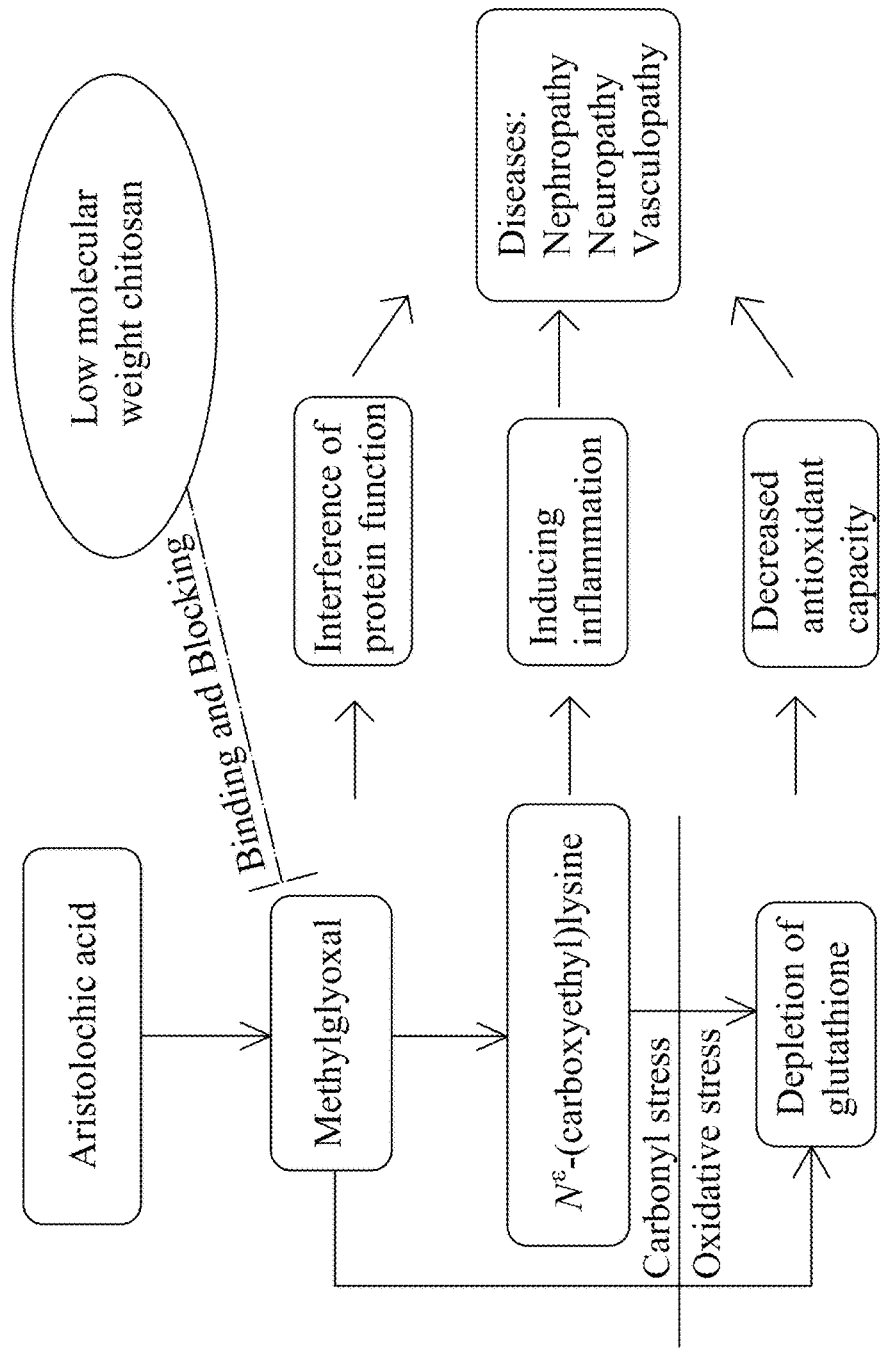
FIG. 5 illustrates a pathogenic mechanism, by which methylglyoxal accumulation leads to disease and serves as a target for low-molecular-weight chitosan binding.

Exemplary Embodiment 8: Hypothetical Scheme for the Role of Low-Molecular-Weight Chitosan in Disease Prevention FIG. 5 illustrates a pathogenic mechanism, by which methylglyoxal accumulation leads to disease and serves as a target for low-molecular-weight chitosan binding. Initially, elevated levels of methylglyoxal and advanced glycation end products cause significant carbonyl stress in aristolochic acid-injected mice and in diseases such as nephropathy, neuropathy and vasculopathy. Subsequent administration of low-molecular-weight chitosan can successfully reverse the increase in methylglyoxal and advanced glycation end products levels. Notably, the anti-carbonyl stress capability in consequence of reversal of methylglyoxal and methylglyoxal-derived advanced glycation end products build-up by low-molecular-weight chitosan is the key pathogenic mechanism of this treatment against diseases such as nephropathy, neuropathy and vasculopathy.

For protective mechanism of low-molecular-weight chitosan, it can block methylglyoxal and led the content level of advanced glycation end products such as $N^e$-(carboxyethyl)lysine decreased, and further improve the damage that methylglyoxal and advanced glycation end products cause like protein dysfunction and inflammation. Carbonyl stress and oxidative stress have interaction and often enhance each other. Notably, the role of low-molecular-weight chitosan on carbonyl stress is more vital than that on oxidative stress.

With foregoing exemplary embodiments, low-molecular-weight chitosan can reduce the accumulation of methylglyoxal and advanced glycation end products. Moreover, low-molecular-weight chitosan can successfully treat severe kidney diseases. In an exemplary embodiment, the conjugation bonding duration of the low-molecular-weight chitosan with methylglyoxal reaches to 24 hours under temperature 37 degree centigrade. Furthermore, low-molecular-weight chitosan can substantially reduce the accumulated level of methylglyoxal and the advanced glycation end products in the kidney of the aristolochic acid nephropathy mouse. Therefore, low-molecular-weight chitosan can effectively protect kidney by reducing carbonyl stress incurred from methylglyoxal.

Besides, for the mouse model in the exemplary embodiment of the present invention, low-molecular-weight chitosan can effectively improve clinical chemical parameters associated with renal function failure. As shown in attached Table-1, it collects all data of improved parameters for renal function of the experiment mice. Obviously, after having treated with suitable quantity of low-molecular-weight chitosan to the aristolochic acid nephropathy mice, all clinical chemical parameters such as urinary microalbumin, serum creatinine, blood urea nitrogen (also known as BUN) and urinary N-acetyl-β-glucosaminidase (also known as NAG) are beneficially varied.

As shown in attached Table-1, the experiment mice are grouped and treated as below: Group C denotes to control group, whose mice are normally controlled for comparative contrast; Group A denotes to disease group, whose mice are treated with aristolochic acid to be infected by the aristolochic acid nephropathy; Group M denotes to low-molecular-weight chitosan group, whose mice are treated with low-molecular-weight chitosan only; and Group AM denotes to therapy group, whose mice are treated with low-molecular-weight chitosan after aristolochic acid nephropathy having infected. Wherein, the parameters of urinary microalbumin, creatinine clearance (also known as Ccr), blood urea nitrogen (BUN) and urinary N-acetyl-β-glucosaminidase (NAG) for the aristolochic acid nephropathy mice in disease group (Group A) are worsen while all foregoing parameters for mice in the therapy group (Group AM) are favorably reversed.

TABLE 1

The improving effect for low-molecular-weight chitosan to kidney function of the experimented mice in vivo

| | Group | | | |
|---|---|---|---|---|
| | Group C | Group A | Group AM | Group M |
| Urinary Microalbumin $(mg \cdot dL^{-1})/$ Ucr $(mg \cdot dL^{-1})$ | 0.47 ± 0.07 | 31.39 ± 2.49* | 25.85 ± 1.20# | 1.48 ± 0.17# |
| Creatinine Clearance (Ccr) $(mL \cdot min^{-1} \cdot kg^{-1})$ | 10.32 ± 0.79 | 2.19 ± 0.29* | 6.15 ± 0.86# | 7.44 ± 1.44# |
| BUN $(mg \cdot dL^{-1})$ | 24.25 ± 1.70 | 117.94 ± 6.70* | 94.76 ± 7.12# | 25.86 ± 0.80# |
| Urinary NAG U/Ucr $(mg \cdot dL^{-1})$ | 122.77 ± 7.31 | 388.89 ± 18.82* | 240.04 ± 27.71# | 162.02 ± 23.27# |

In attached Table-1, some remarks are further expressed as below. The word "Ucr" denotes to meaning of the "Urinary Creatinine". The character "*" denotes p<0.05 comparing to control group (C). The character "#" denotes p<0.05 comparing to control group (C), Where n=6.

Besides, interpretation of the Table-1 is elucidated in following paragraphs.

As shown in attached Table-1, data of urinary microalbumin for every group reflect following facts. The data of urinary microalbumin for Group C is 0.47±0.07 [mg·dL$^{-1}$]/Ucr [mg·dL$^{-1}$], p<0.05; the data of urinary microalbumin for Group A is 31.39±2.49 [mg·dL$^{-1}$]/Ucr [mg·dL$^{-1}$]; and the data of urinary microalbumin for Group AM is 25.85±1.20 [mg·dL$^{-1}$]/Ucr [mg·dL$^{-1}$]. Apparently, the urinary microalbumin of Group A is much higher than that of Group C while the urinary microalbumin of Group AM is lower than that of Group A, which means the treatment of low-molecular-weight chitosan has favorable reversing effect for the data of urinary microalbumin.

Moreover, as shown in attached Table-1, data of creatinine clearance (Ccr) for every group reflect following facts. The data of creatinine clearance for Group C is 10.32±0.79 mL·min$^{-1}$·kg$^{-1}$, p<0.05; the data of creatinine clearance for Group A is 2.19±0.29 mL·min$^{-1}$·kg$^{-1}$; and the data of creatinine clearance for Group AM is 6.15±0.86 mL·min$^{-1}$·

$kg^{-1}$, $p<0.05$. Apparently, the creatinine clearance of Group A is lower than that of Group C while the creatinine clearance of Group AM is higher than that of Group A, which means the treatment of low-molecular-weight chitosan has favorable reversing effect for partially recovering data of creatinine clearance.

Furthermore, as shown in attached Table-1, data of blood urea nitrogen (BUN) for every group reflect following facts. The data of blood urea nitrogen for Group C is $24.25\pm1.70$ mg·dL$^{-1}$, $p<0.05$; the data of blood urea nitrogen for Group A is $117.9\pm6.70$ mg·dL$^{-1}$; and the data of blood urea nitrogen for Group AM is $94.76\pm7.12$ mg·dL$^{-1}$, $p<0.05$. Apparently, the blood urea nitrogen of Group A is much higher than that of Group C while the blood urea nitrogen of Group AM is lower than that of Group A, which means the treatment of low-molecular-weight chitosan has favorable reversing effect for partially reducing data of blood urea nitrogen.

Besides, as shown in attached Table-1, data of N-acetyl-β-glucosaminidase (NAG) for every group reflect following facts. The data of N-acetyl-β-glucosaminidase for Group C is $122.77\pm7.31$ U/Ucr [mg·dL$^{-1}$], $p<0.05$; the data of N-acetyl-β-glucosaminidase for Group A is $388.89\pm18.82$ U/Ucr [mg·dL$^{-1}$]; and the data of N-acetyl-β-glucosaminidase for Group AM is $162.02\pm27.71$ U/Ucr [mg·dL$^{-1}$], $p<0.05$ vs. Group A mice. Apparently, the N-acetyl-β-glucosaminidase of Group A is much higher than the that of Group C while the N-acetyl-β-glucosaminidase of Group AM is lower than that of Group A, which means the treatment of low-molecular-weight chitosan for 14 days has favorable reversing effect for partially reducing data of N-acetyl-β-glucosaminidase.

Notably, all favorable effects in the treatment of low-molecular-weight chitosan are caused by the pathogenic molecular mechanism thereof. For example, glutathione is required to serve as cofactor for excluding methylglyoxal in glyoxalase system. All data in exemplary embodiments of the present invention reflect that the content level of glutathione is exhausted during renal damaging process, which probably causes accumulation of methylglyoxal. However, the treatment of low-molecular-weight chitosan is not able to reverse the exhaust of the glutathione. All previous studies believe that low-molecular-weight chitosan may involve in reducing oxidative stress. However, all data in exemplary embodiments of the present invention reflect that the renal protective feature of low-molecular-weight chitosan and methylglyoxal reducing feature of low-molecular-weight chitosan has mutually dependence to each other, but the of low-molecular-weight chitosan is probably independent of renal anti-oxidative activity.

Foregoing exemplary embodiments of the present invention manifest that the low-molecular-weight chitosan has considerable effect to the carbonyl stress induced by the methylglyoxal both in vivo and in vitro. For an exemplary embodiment in vitro, the present invention employs buffer to simulate the same environmental status as human body by means of putting glucosamine and low-molecular-weight chitosan into buffer containing methylglyoxal to measure the bonding ratio thereof after 16 hours so that the half Inhibitory concentration associated with the affecting of low-molecular-weight chitosan to methylglyoxal can be obtained for further study on the examination of the binding conjugation of low-molecular-weight chitosan with methylglyoxal in vitro. For another exemplary embodiment in vivo, a mouse model of aristolochic acid-induced nephropathy is applied to assay whether low-molecular-weight chitosan can reduce renal level of methylglyoxal, which exhibits 12-fold greater accumulation of methylglyoxal in the kidneys than that found in controlled normal mice.

From foregoing exemplary embodiments of the present invention, binding conjugation of low-molecular-weight chitosan with methylglyoxal in vitro demonstrated that the concentration of low-molecular-weight chitosan required to achieve 50% inhibition is 4.60 µg mL$^{-1}$. Other than that, the binding conjugation of low-molecular-weight chitosan with methylglyoxal in vitro is greater than that of metformin, which is the only one effective methylglyoxal reducing agent has been approved by the US Food and Drug Administration (FDA) to date. In mouse model of aristolochic acid-induced nephropathy, treatment with low-molecular-weight chitosan (500 mg kg$^{-1}$ day$^{-1}$ orally) for 14 days, the renal methylglyoxal accumulation is significantly reduced from $212.86\pm24.34$ down to $86.15\pm33.79$ µg g$^{-1}$ protein ($p<0.05$) such that the reducing ratio thereof is over 55% in the aristolochic acid-induced nephropathy model. Moreover, and the level of advanced glycation end products in the kidney of aristolochic acid nephropathy mouse is significantly reduced from $4.60\pm0.27$ down to $2.84\pm0.28$ µmol µg$^{-1}$ protein ($p<0.05$) such that the reducing ratio thereof is over 35% in the aristolochic acid-induced nephropathy model.

These data suggest that low-molecular-weight chitosan might represent a novel treatment modality for methylglyoxal-related diseases. Previously, no study about using monosaccharides and/or polysaccharides to produce pharmaceutical composition with feature in reducing methylglyoxal is found or disclosed. Apparently, with our foregoing disclosures heretofore, monosaccharides and/or polysaccharides indeed have preventive or treatment features for nephropathy, diseases incurred by pathogenesis associated with methylglyoxal or diseases induced by carbonyl stress such as partial aging process in human body, liver disease, kidney disease, heart disease, arthritis, diabetic complications, cataract, chronic renal failure and cancer. Other than that, monosaccharides and/or polysaccharides can also be used to produce pharmaceutical composition with same preventive or treatment features as mentioned above.

The foregoing description of the preferred embodiment of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary limited the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A method of treating a patient with a disease caused by a pathogenic mechanism associated with accumulation of methylglyoxal, the method comprising:
    administering an effective amount of chitosan to the patient suffering from the disease to reduce a content level of methylglyoxal in the patient, wherein the disease is selected from the group consisting of arthritis and cataract, wherein said chitosan has a range of molecular weight from 29 kDa to 36 kDa.

2. The method according to claim 1, wherein the effective amount of the chitosan is 87.52 mg $kg^{-1}$ $day^{-1}$.

* * * * *